(12) United States Patent
Maalej et al.

(10) Patent No.: US 11,116,462 B2
(45) Date of Patent: Sep. 14, 2021

(54) X-RAY SYSTEM AND METHOD FOR GENERATING X-RAY IMAGE IN COLOR

(71) Applicant: KING FAHD UNIVERSITY OF PETROLEUM AND MINERALS, Dhahran (SA)

(72) Inventors: Nabil Mohammed Maalej, Dhahran (SA); Fahad Ahmad Abozaid, Khobar (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 26 days.

(21) Appl. No.: 16/114,357

(22) Filed: Aug. 28, 2018

(65) Prior Publication Data
US 2020/0069271 A1    Mar. 5, 2020

(51) Int. Cl.
*A61B 6/03* (2006.01)
*A61B 6/00* (2006.01)
(Continued)

(52) U.S. Cl.
CPC .............. *A61B 6/482* (2013.01); *A61B 6/405* (2013.01); *A61B 6/4042* (2013.01);
(Continued)

(58) Field of Classification Search
CPC ....... A61B 6/482; A61B 6/4042; A61B 6/405; A61B 6/4241; A61B 6/542; A61B 6/563;
(Continued)

(56) References Cited

U.S. PATENT DOCUMENTS 4,433,431 A * 2/1984 Pfeiler .................... H01J 35/10
378/124
6,973,158 B2  12/2005  Besson
(Continued)

OTHER PUBLICATIONS

"Amptek Mini-X X-Ray Tube Application Note Filters on an X-Ray Tube", Ametek Materials Analysis Division, www.amptek.com, Jun. 10, 2015, 4 pages.
(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

A method for generating an x-ray image in color includes selecting three-sets of x-ray images in gray scale acquired with x-rays having different energy spectra, assigning basic colors RGB to the three-sets, and displaying the x-ray image in color with RGB signals generated. A system for generating an x-ray image in color includes an x-ray generator configured to generate at least three sets of x-rays with different energy spectra, an x-ray detector, a controller, a computer, and a color display. The computer is configured to generate three sets of x-ray images from output data of the x-ray detector acquired for x-rays with different energy spectra, assign RGB and display an x-ray image in color. A non-transitory computer readable medium stores an instruc-
(Continued)

tion, when the instruction is executed by a processor, cause the processor to perform the method for generating an x-ray image in color.

7 Claims, 14 Drawing Sheets

(51) Int. Cl.
    *G06T 5/50*     (2006.01)
    *H01J 35/10*     (2006.01)
    *H01J 35/06*     (2006.01)

(52) U.S. Cl.
    CPC ............ *A61B 6/4241* (2013.01); *A61B 6/542* (2013.01); *A61B 6/563* (2013.01); *G06T 5/50* (2013.01); *H01J 35/101* (2013.01); *A61B 6/463* (2013.01); *G06T 2207/10116* (2013.01); *H01J 35/065* (2013.01)

(58) Field of Classification Search
    CPC . A61B 6/463; G06T 5/50; G06T 2207/10116; H01J 35/101; H01J 35/065
    See application file for complete search history.

(56) References Cited

U.S. PATENT DOCUMENTS

| | | | |
|---|---|---|---|
| 2004/0013225 A1* | 1/2004 | Gregerson | A61B 6/4452 378/19 |
| 2005/0084073 A1 | 4/2005 | Seppi et al. | |
| 2005/0190882 A1 | 9/2005 | McGuire | |
| 2009/0129544 A1* | 5/2009 | Chen | G01N 23/087 378/62 |
| 2012/0127174 A1* | 5/2012 | Naidu | G06T 11/001 345/419 |
| 2014/0276085 A1* | 9/2014 | Miller | A61B 8/483 600/467 |
| 2018/0333109 A1* | 11/2018 | Zamenhof | A61B 6/4042 |

OTHER PUBLICATIONS

"Typical X-ray Spectra by Anode Material", Oxford Instruments, The Business of Science, Mar. 6, 2015, 5 pages.

\* cited by examiner

X-RAY SYSTEM AND METHOD FOR GENERATING X-RAY IMAGE IN COLOR

BACKGROUND

Technical Field

The present disclosure relates to generation, detection and processing of x-rays and more particularly to a method for generating x-ray images in color, by processing x-ray images in gray scale acquired with x-rays with different energy spectra.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

An x-ray tube that produces x-rays in the diagnostic energy range typically contains an electron source, an evacuated path for electron acceleration, a target electrode, and an external power source to provide an accelerating voltage to accelerate the electrons. The x-rays generated from the x-ray tube typically have two principal components. One is a continuous spectrum known as bremsstrahlung spectrum, and the other is the characteristic x-rays exhibiting sharp peak(s) at wavelengths specific to material of the target electrode.

Interactions of the x-rays with matter under diagnostics include Rayleigh scattering, Compton scattering, and photoelectric absorption. Rayleigh scattering causes slight deflections of x-rays but no energy shift. Compton scattering causes both energy shift and large deflections of x-rays. In photoelectric absorption, an incident photon energy is completely absorbed to eject a valence electron at a deep level of an atom, where simultaneously, characteristic x-rays from the atom that absorbed the incident photon energy may be emitted by transitions of upper level valence electrons to the deep level. Photoelectric absorption causes attenuation of x-rays and possible generation of characteristic x-rays but no scattering, thus dominantly contributes to formation of x-ray images. X-rays traversed the matter under diagnostics are detected including scattered x-rays to form an x-ray image conventionally, where the scattered x-rays have deleterious effect on image quality.

Pixel values of a digital detector for recent medical use have bit depth up to 14 bits (16,384 shades of gray), while modern displays are only capable of displaying up to 10 bits (1,024 shades of gray). Thus, various mapping of pixel values to light intensity of the display called look up table (LUT) are adopted to optimize the contrast of important features in the image, including leveling which determines a pixel value corresponding to the mid-point of the display and windowing which determines the range of the pixel values to be displayed (see for example "The Essential Physics of Medical Imaging," 3rd ed., 2012, ISBN 978-0-7817-8057-5, J. T. Bushberg, J. A. Seibelt, E. M. Leidholdt Jr, and J. M. Boone, LIPPINCOTT WILLIAMS & WILKINS, the entire contents of which are incorporated herein by reference).

The selective generation of either "soft" x-rays with energies around 20 KeV for use in mammography or "hard" x-rays with much higher energies for conventional purposes with an x-ray tube comprising a rotating target electrode with a first anode made of tungsten and a second anode made of molybdenum, rhodium, silver, or palladium was described in "Rotating-Anode X-ray Tube with Multiple Focal Areas," Y. Seki and K. Tanabe, U.S. Pat. No. 3,610,984, the entire contents of which are incorporated herein by reference.

Producing x-rays with a spectrum selectable from a plurality of specific different wavelength spectra by bombarding an array of primary targets of different composition with an electron beam directable to any one of the array, and by further combining a secondary target selectable from a plurality of differing compositions and aligned to absorb generated x-rays and to emit characteristic x-rays was described in "Selectable Wavelength X-ray Source, Spectrometer and Assay Method," R. D. Albert, U.S. Pat. Nos. 3,925,660 and 4,048,496, the entire contents of which are incorporated herein by reference.

Generating x-rays at different energy levels by combinations of targets of different materials and filters placed between the targets and a body under examination, detecting the x-rays to obtain a plurality of image data of the body at the different energy levels, and enhancing or maximizing an appearance of a feature due to a contrast agent in a contrast image by integrating or subtracting the image data at different energy levels was described in "Multi-energy x-ray source," E. Seppi and G. Virshup, U.S. Pat. No. 7,649,981, the entire contents of which are incorporated herein by reference.

Acquiring a plurality of sets of image data with x-rays generated by a wideband source and filtration assembly, and analytical processing of the plurality sets of image data including decomposition to basis functions to facilitate computer assisted diagnostics was described in "Dynamic multi-spectral CT imaging," G. M. Besson, U.S. Pat. No. 6,950,493 and "Multi-target X-ray tube for dynamic multi-spectral limited-angle CT imaging," U.S. Pat. No. 6,973,158, the entire contents of which are incorporated herein by reference.

Superimposing a nuclear medicine image in color on a gray scale x-ray CT image was described in "The Essential Physics of Medical Imaging," pp. 131-132, 3rd ed., 2012, ISBN 978-0-7817-8057-5, J. T. Bushberg, J. A. Seibelt, E. M. Leidholdt Jr, and J. M. Boone, LIPPINCOTT WILLIAMS & WILKINS, the entire contents of which are incorporated herein by reference.

It is an object of the present disclosure to disclose methods and systems of directly or digitally converting x-ray images obtained in grey scale to provide corresponding multi-color images, in particular by comparison of a plurality of greyscale images obtained using x-rays of a plurality of different energy spectra.

SUMMARY

In an exemplary embodiment, a method for generating an x-ray image in color includes acquiring at least three-sets of x-ray images of a body under examination in gray scale for x-rays with different energy spectra, selecting three-sets of x-ray images, assigning red (R), green (G), and blue (B) to the three-sets of x-ray images, and displaying the x-ray image in color with RGB signals generated based on an assignment of RGB to the three-sets of x-ray images. The method also includes selecting a weighting of RGB signals, and storing information on the x-ray image in color with a selected weighting of RGB signals.

In another exemplary embodiment, a system for generating an x-ray image in color includes an x-ray generator configured to generate a plurality sets of x-rays with different energy spectra, an x-ray detector, a controller configured to control the x-ray generator and the x-ray detector, a computer configured to communicate with the controller, and a color display. The controller is configured to acquire output data from the x-ray detector corresponding to each of a plurality sets of x-rays with different energy spectra and to generate the plurality sets of x-ray images in gray scale. The computer is further configured to select three-sets of x-ray images and display the x-ray image in color on the color display. The system of generating color x-ray can be implemented in any of the digital x-ray imaging systems including radiography, mammography, fluoroscopy, angiography, computer tomography (CT), x-ray security scanners of language at airports, etc.

In another exemplary embodiment, instructions are stored in a non-transitory computer readable medium. The instruction, when executed by a processor, cause the processor to perform the method for generating an x-ray image in color from at least three sets of x-ray images in gray scale acquired for x-rays with different energy spectra.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
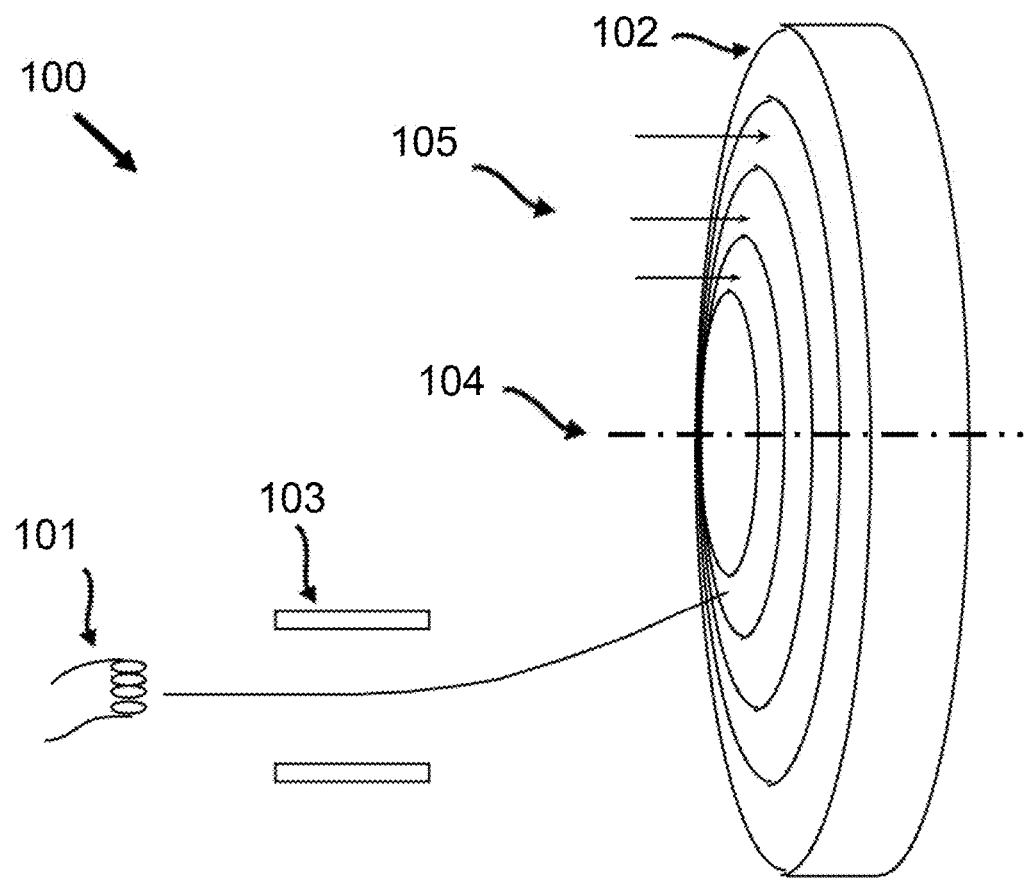
FIG. 1 illustrates an x-ray tube comprising a cathode, an anode with anode tracks constructed from different target materials and control plate according to certain embodiment of the present disclosure.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to method for generating x-ray images at three or more different x-ray energies and processing and displaying those x-ray images as color images.

X-ray images have conventionally been thought not to benefit from being displayed in color, and are therefore commonly displayed for interpretation in gray scale, even with high-quality monitors. On the other hand, in the field of nuclear medicine, color image display has been widely adopted. For example, "false color images" are displayed, where starting from a single image acquired in nuclear medicine technology, a color image is displayed with artificial or synthesized RGB signals created with independent translation tables. Myocardial perfusion images from a gamma scintillator can be superimposed on a grayscale x-ray CT image based on image co-registration technique. However, securing a spatialy congruency between images using a technique called image co-registration is required when image data from one medical imaging modality is superimposed on image data from another modality. Spatial miss-registration between the two images often causes errors in attenuation coefficients, and results in generation of artifacts see for example "The Essential Physics of Medical Imaging," pp. 117-132, Id, the entire contents of which are incorporated herein by reference).

FIG. 1 illustrates an x-ray tube 100 comprising a cathode 101, an anode 102 with anode tracks 105 made from different target materials and control plates 103 according to an embodiment of the present disclosure. The control plates 103 are aligned between the cathode 101 and the anode 102 to deflect electron beams from the cathode 101 using an electric and/or magnetic field so that any one of the different anode tracks can be selected by a control signal $V_c$ which is not illustrated but can be configured to be applied to the control plates 103 to produce different x-ray spectra, e.g., x-ray spectra of different intensity or spectral distribution. The electron beams can be also deflected circularly about the center axis 104 of the anode 102, and along the target tracks 105 in response to variations of the control signal $V_c$. The materials for the anode tracks 105 comprise at least one of three different high Z-materials, preferably tungsten, molybdenum, or rhodium. Other high Z materials include those metallic elements having a similarly high number of protons in the nucleus, preferably a second or third row transition metal. X-ray spectra can also be modified by varying the acceleration voltage $V_p$ which is not shown here, supplied between the cathode 101 and the anode 102. Depending on the acceleration voltage $V_p$, characteristic x-rays unique to the target material may appear in addition to the bremsstrahlung spectrum.

In FIG. 1, the anode tracks 105 are shown in a circumferential orientation as nested circles. Other configurations may be used such that anode tracks made from different target materials are arranged in a grid or horizontal/vertical stripe fashion. The anode tracks may comprise a mixture of target materials in different proportions. For example, one or more anode tracks may contain two or more target materials in a weight ratio of 1:10, preferably 2:8, 4:6, or 1:1 based on the weights of the two target materials. In embodiments, anode tracks may be constructed of different target materials to provide a tailored x-ray spectrum that may contain a number of photoelectric emission peaks. In a preferable embodiment at least one anode track contains a mixture of target materials with emission peaks that do not overlap, such as a combination of tungsten and molybdenum where major emission peaks correspond to both tungsten and molybdenum narrow photoelectric peaks.

Figure 2:
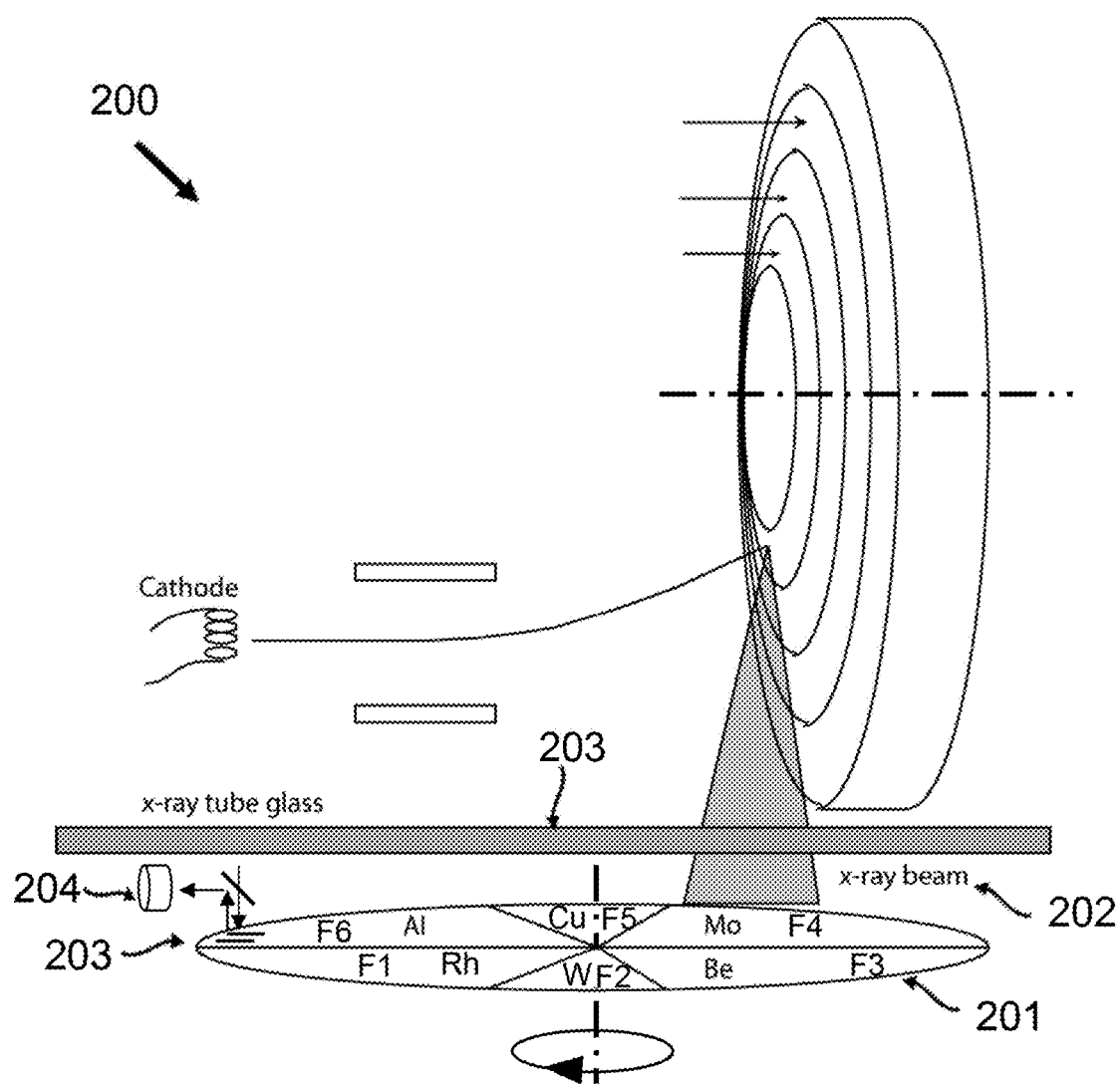
FIG. 2 illustrates an x-ray tube aligned with a filter wheel with filter sectors made of different filter materials with different thickness to provide different filtration of the x-rays emitted from an anode of the x-ray tube under certain embodiment of the present disclosure.

FIG. 2 illustrates an x-ray tube 200 comprising similar elements to those of FIG. 1, but further comprising a filter wheel 201 with filter sectors F1 to F6 made of different filter materials with different thickness to provide different filtration of the x-ray spectra under certain embodiment of the present disclosure. The x-rays 202 generated from the anode and emitted through x-ray tube glass 203 are configured to pass through one of the filter sectors of the filter wheel, where the filter sector is selected to generate x-rays with three or more different energy spectra required for a diagnostic purpose. The filter materials preferably comprise at least one of tungsten, molybdenum, rhodium, copper, aluminum, or beryllium, but other alkali, alkaline earth and transition metals may be used. The filter materials may be selected to utilize k-edge energies in absorption spectra to generate very different spectra. The filter wheel 201 is configured rotatably around an axis by driving with a digital servo motor not illustrated here, where rotation frequency of the filter wheel 201 is measured and controlled by detecting a reflection of light from a marker 203 by a photo detector 204. Thus, a plurality sets of x-rays with different energy spectra can be generated in high speed by synchronously choosing a combination of one or more target tracks to which the electron beams are impinged and one or more of the filter sections, while the filter wheel 201 keeps rotating in controlled manner. The x-ray machine may have a controller (not illustrated) that selects a combination of anode materials, filter material and tube voltages to generate three or more consecutive fast exposures at different energy spectra. The images corresponding to each energy spectrum are automatically combined to generate a color x-ray image.

Figure 3:
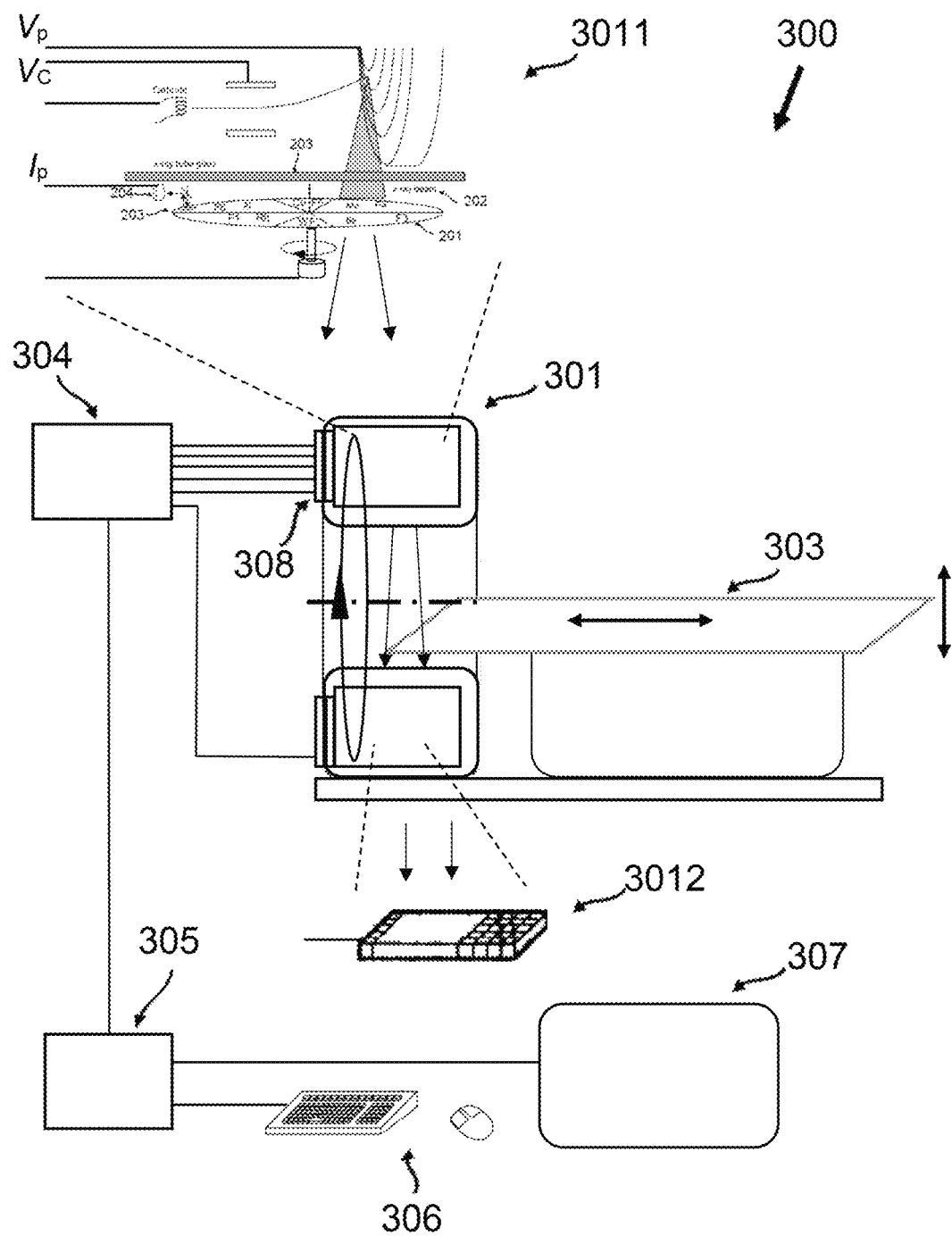
FIG. 3 is an exemplary diagram of an x-ray or CT diagnostic imaging system configured to be capable of acquiring attenuation data for x-rays with three or more different energy spectra, under certain embodiment of the present disclosure.

FIG. 3 is an exemplary diagram of an x-ray CT diagnostic system 300 configured to be capable of acquiring attenuation data for x-rays with three or more different energy spectra, according to an embodiment of the present disclosure. Included are preferably a gantry housing 301 having a shape like a torus and fixed to a base, a patient table 303 configured to be movable to align a patient at a center of a bore of the gantry housing, a controller 304, a computer 305, human interfaces 306, and a color display. The gantry housing 301 includes inside an x-ray generator 3011 described in FIG. 2, and an x-ray detector 3012 aligned to detect x-rays emitted from the x-ray generator after having traversed a body under examination, where both or at least the x-ray generator is configured rotatably inside the gantry housing around a center axis of the gantry housing. A slip-ring 308 secures electrical connections between the controller 304 aligned outside to be stationary and devices inside of the gantry housing that rotate in high speed.

Figure 4:
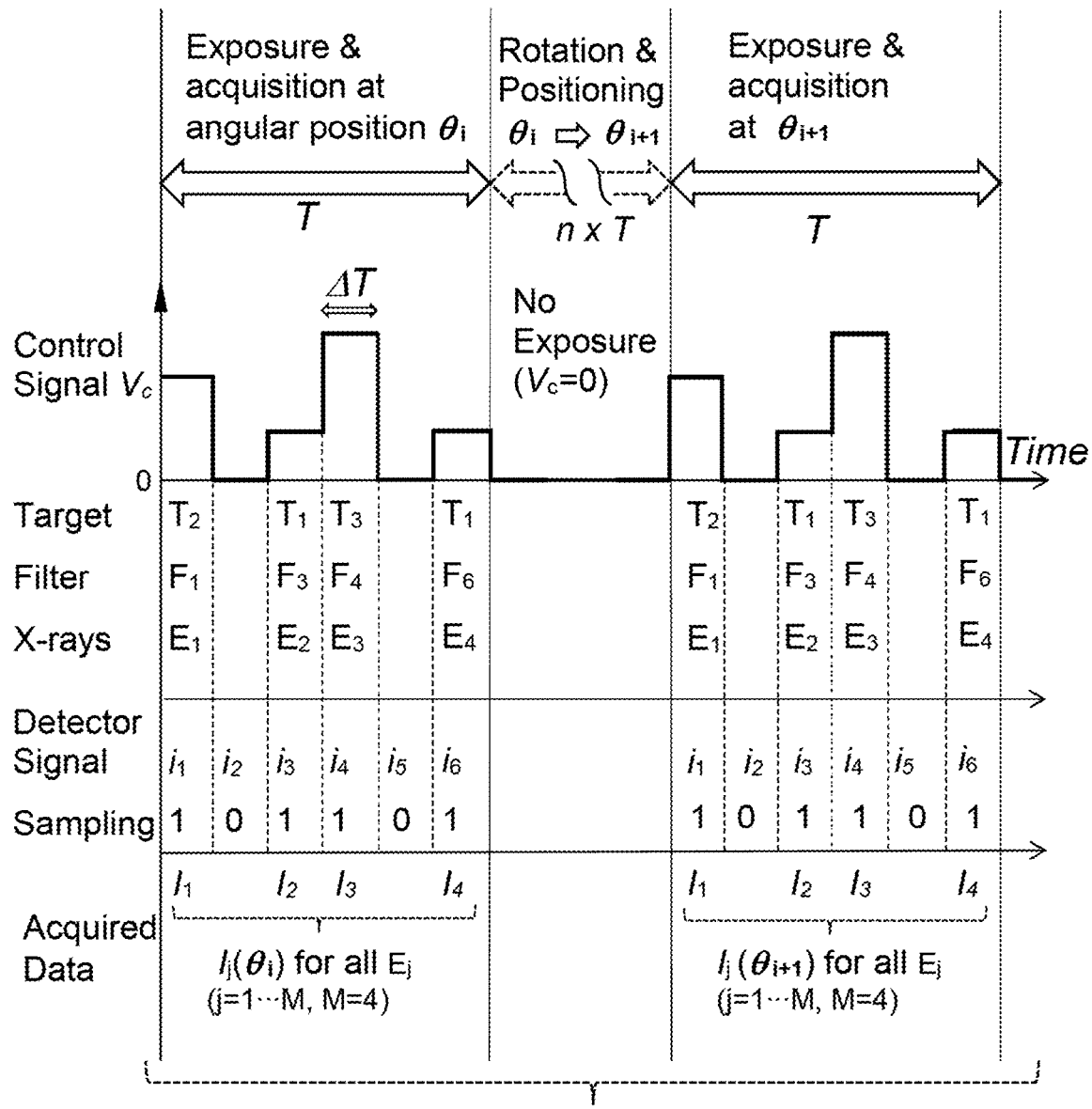
FIG. 4 is an exemplary time chart to generate a plurality sets of x-rays with different energy spectra and to acquire corresponding x-ray attenuation data for the plurality sets of CT images in a speed high enough to be adopted in conventional x-ray CT diagnostics, under certain embodiment of the present disclosure.

FIG. 4 illustrates an exemplary time chart to generate a plurality of sets of x-rays with different energy spectra and to acquire corresponding x-ray attenuation data in order to generate a plurality of sets of CT images in the x-ray CT diagnostic system described in FIG. 3, according to an embodiment of the present disclosure. In FIG. 4, time durations of Exposure & Acquisition at $\theta_i$ and at $\theta_{i+1}$, Rotation & Positioning are chosen equivalent to those steps in conventional x-ray measurement for CT diagnostics. A measurement period T for the Exposure and Acquisition at each of the angular positions is set to be the same as, that is, synchronized with a rotation period of the filter wheel. On the other hand, a time for the Rotation and Positioning is set integer n times of the measurement period T, where the measurement period T is in same order as one for the conventional x-ray CT. During the measurement period T, each of the filter sectors F1 to F6 has a chance of x-ray exposure for a filter sector exposure period $\Delta T$ for each. Thus, a control signal $V_c$ is controlled synchronously to choose combinations of the target materials and the filter sectors required to generate x-rays with planned energy spectra, and to avoid an exposure to those filter sectors that are unnecessary for the planned energy spectra. An x-ray detector configured to detect x-rays after passing the body under examination, not illustrated, functions to detects x-rays at a sampling period corresponding to exposures of each of the filter sectors F1 to F6. Detector signals $i_1$ to $i_6$ are transferred to a random access memory in the controller 304 and stored. Thereafter, during the following Rotation and Positioning period, effective detector signals corresponding to the filter sectors that x-rays E1 to E4 were actually exposed (F1, F3, F4 and F6 in this example) are further sampled by referring to the control signal $V_c$, and stored as Acquired Data $I_1(\theta_i)$ to $I_4(\theta_i)$ at angular position $\theta_i$ and for four sets of different energy x-rays spectra $E_1$ to $E_4$. Similar procedures are repeated after Rotation and Positioning at the angular position where acquired data will be $I_1(\theta_i)$ to $I_4(\theta_i)$ for the same four sets of different energy spectra. By repeating the above procedure for all circumference angular positions with a required step $\Delta\theta$, permits acquisition of all x-ray absorption data required for CT image processing. Then, based on conventional tomography data processing, a plurality of sets of x-ray CT images at different energy spectra $E_1$ to $E_4$ are obtained. A filtered back-projection or other CT image reconstruction technique would then be used to reconstruct CT gray scale images corresponding to at least 3 energy spectra E1, E2, E3. The three or more gray scale images are then automatically combined to generate a color image. In the color image, the different regions of CT numbers (related to tissue or material attenuation coefficients) would have distinctively different colors and different, shades of colors instead of a conventional gray scale image.

As described above, x-ray exposures and data acquisitions for different energy spectra at certain angular values are completed within the measurement period, that is, a time duration spent in conventional x-ray CT measurement at a certain angular position. This fast data acquisition feature enables acquisition of a plurality of sets of CT images for x-rays for different energy spectra within the scanning time used for obtaining a conventional CT image. The feature also enables co-registration of images acquired for x-rays with different energy spectra, by avoiding the spatial misregistration problem which may cause the artifacts generation as described earlier.

sure (see J. A. Bearden and Burr, "X-Ray Wavelengths," Rev. Mod. Phys. 39 125, 1967, and "X-ray Absorption Edge Energies," B. Rupp, http://www.ruppweb.org/Xray/elements.html,). Referring to Table 1, the Spectrum A for tungsten exhibits characteristic x-rays around 8 to 11 KeV, which correspond to L-lines, and thus the spectrum A (FIG. 5) lacks K-lines because of lower acceleration energy than the K-shell-edge energy as discussed above. On the other hand, the acceleration energies around 35 KeV for spectra B (FIG. 5) (molybdenum) and C (rhodium) are both larger than the K-shell edge energies for both (20 KeV and 23.2 KeV). Thus, characteristic x-rays around 17 to 20 KeV in the spectrum B for molybdenum and those around 20 to 23 KeV in the spectrum C for rhodium all correspond well to K-lines. This correspondence indicates that the tungsten target also exhibits K-line characteristic x-rays around 60 to 67 KeV (Table 1) when the acceleration energy is higher than the K-shell edge energy 69.5 KeV.

The energy of the x-rays may vary in intensity in a range of from 100 eV to 100 KeV, preferably 1 KeV-50 KeV, 5 KeV-25 KeV, or 10 KeV-20 KeV. The x-rays of interest in the present disclosure have a wavelength ranging from 0.1 to 10 nm.

TABLE 1

| Material | | W | Ag | Rh | Mo | Be | Cu | Al |
|---|---|---|---|---|---|---|---|---|
| Characteristic X-ray Energy | $K\alpha 1$ | 59.318 | 22.163 | 20.216 | 14.479 | 0.109 | 8.048 | 1.487 |
| | $K\alpha 2$ | 57.982 | 21.990 | 20.074 | 17.374 | | 8.028 | 1.486 |
| | $K\beta 1$ | 67.240 | 24.942 | 22.724 | 19.608 | | 8.905 | 1.557 |
| | $L\alpha 1$ | 8.398 | 2.984 | 2.697 | 2.293 | | | |
| | $L\alpha 2$ | 8.335 | 2.978 | 2.692 | 2.290 | | 0.930 | |
| | $L\beta 1$ | 9.672 | 3.151 | 2.834 | 2.395 | | 0.930 | |
| | $L\beta 2$ | 9.962 | 3.348 | 3.001 | 2.518 | | 0.950 | |
| | $L\gamma 1$ | 11.286 | 3.520 | 3.144 | 2.624 | | | |
| Absorption Edge Energy | K-edge | 69.525 | 25.514 | 23.220 | 20.000 | 0.111 | 8.979 | 1.560 |
| | L-edge | 10.206 | 3.351 | 3.004 | 2.520 | NA | 1.096 | 0.118 |
| | | 11.544 | 3.523 | 3.146 | 2.625 | | | |
| | | 12.100 | 3.805 | 3.411 | 2.866 | | | |

(Unit: KeV)

Figure 5:
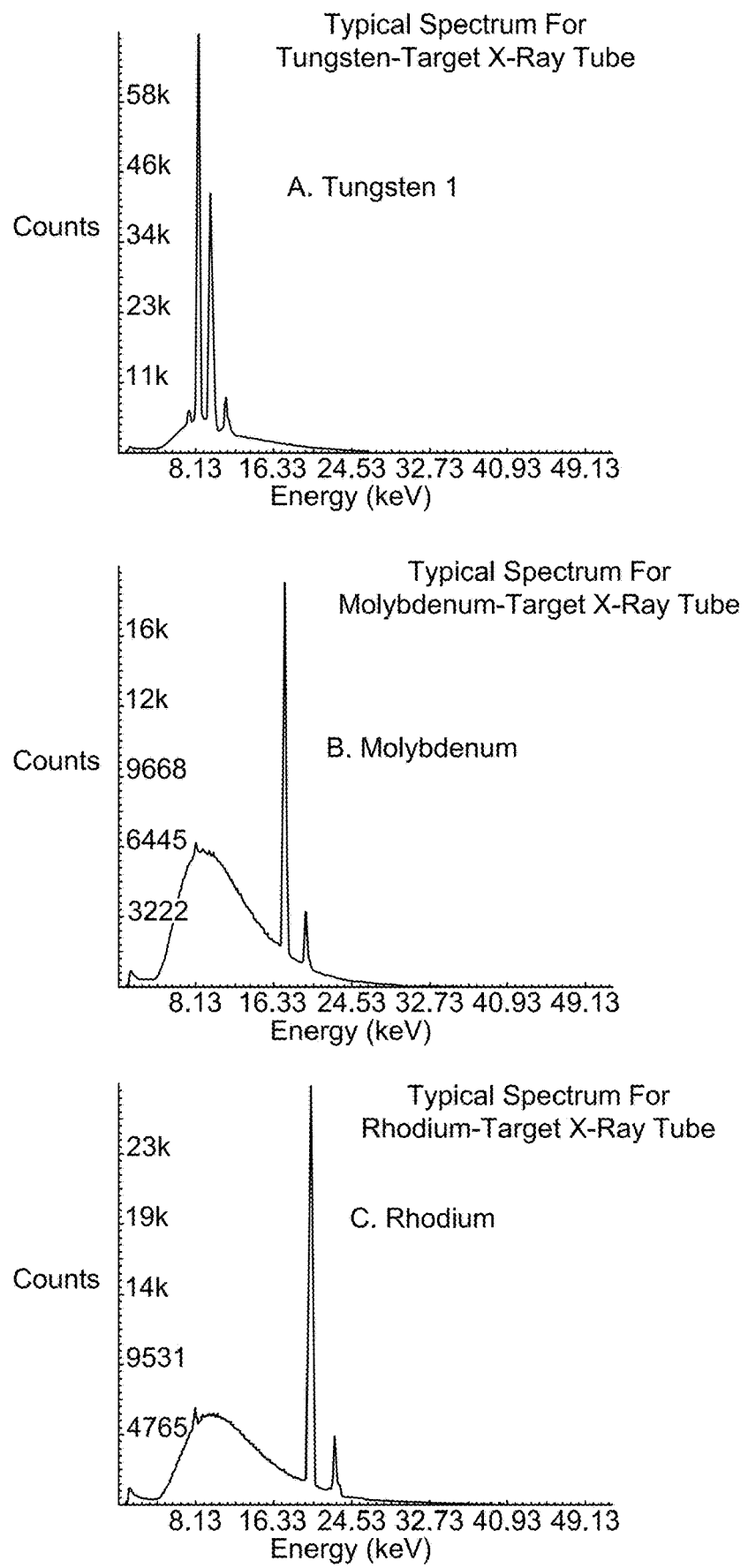
FIG. 5 illustrates exemplary x-ray spectra generated from different target materials, under certain embodiment of the present disclosure.

FIG. 5 illustrates exemplary mammography x-ray spectra generated from different target materials, A, B, and C for tungsten, molybdenum, and rhodium respectively, according to embodiments of the present disclosure (see "Typical x-ray spectra by anode material," Application Note, 2018, Oxford Instruments, the entire contents of which are incorporated herein by reference). Here, the acceleration energy of less than 40 KeV in A for tungsten is lower than a K-shell edge energy 69.5 KeV, while, for B and C, both acceleration energies of over 30 KeV are higher than K-shell edge energies, 20.0 KeV and 23.2 KeV, for molybdenum and rhodium, respectively. Images acquired for three or more different mammography x-ray spectra can be obtained rapidly and in succession to minimize the time of exposure. The three or more images can also be combined to generate color mammography images with color adding to the contrast detectability normally achieved with plane gray scale mammography images. The same techniques can be applied in other x-ray modalities such as digital radiography, fluoroscopy, angiography, x-ray security scanners at the corresponding optimal x-ray spectra for each modality and subject thickness.

Figure 6:
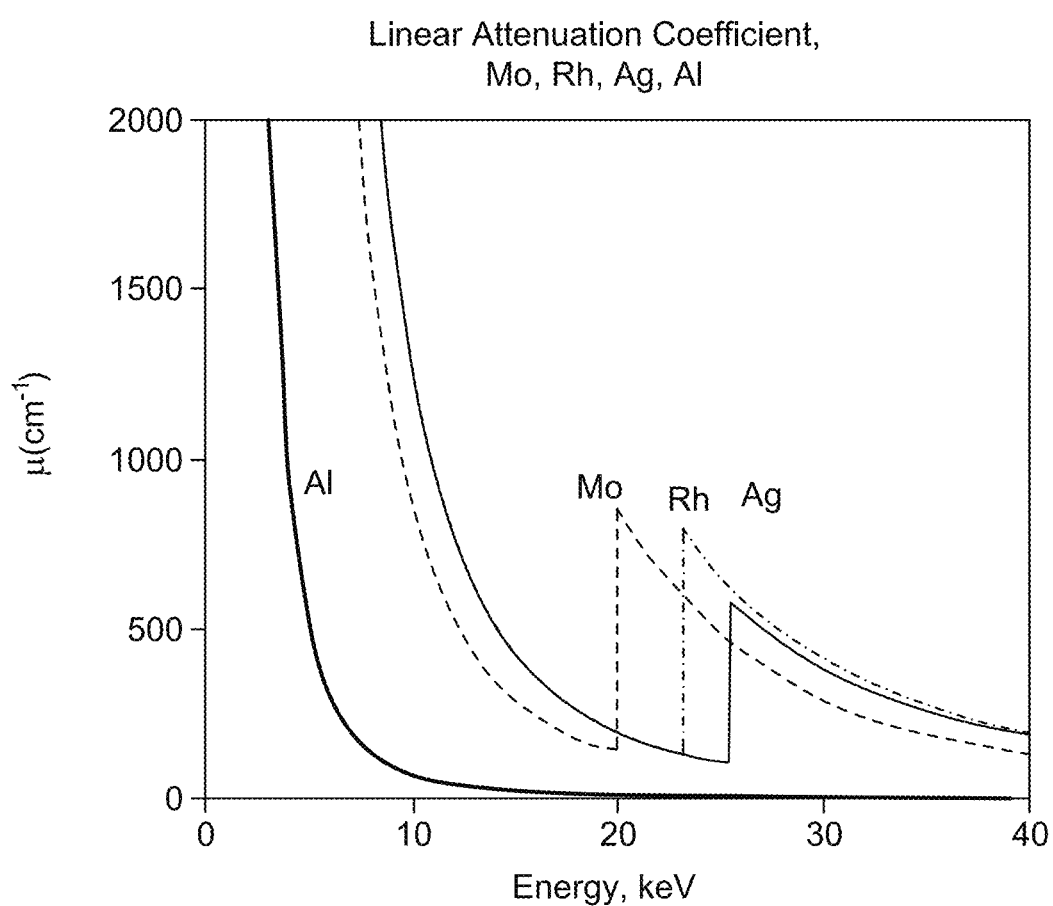
FIG. 6 is an exemplary graph of incident energy dependence of x-ray attenuation coefficients for exemplary filter materials, under certain embodiments of the present disclosure.

Table 1 summarizes characteristic x-ray energies and absorption edge energies for candidate materials as target and filter according to embodiments of the present disclo- FIG. 6 is a graph illustrating incident energy dependence of x-ray attenuation coefficients for exemplary filter materials including aluminum (Al), molybdenum (Mo), rhodium (Rh) and silver (Ag). Energy values where sudden increase of attenuation are observed when incident energy increases all well agree with the K-shell edge energies of the material, summarized in Table 1. Those absorption characteristics of the filter materials can be used to tailor the x-ray spectrum emitted from the x-ray tube, as described below.

Figure 7:
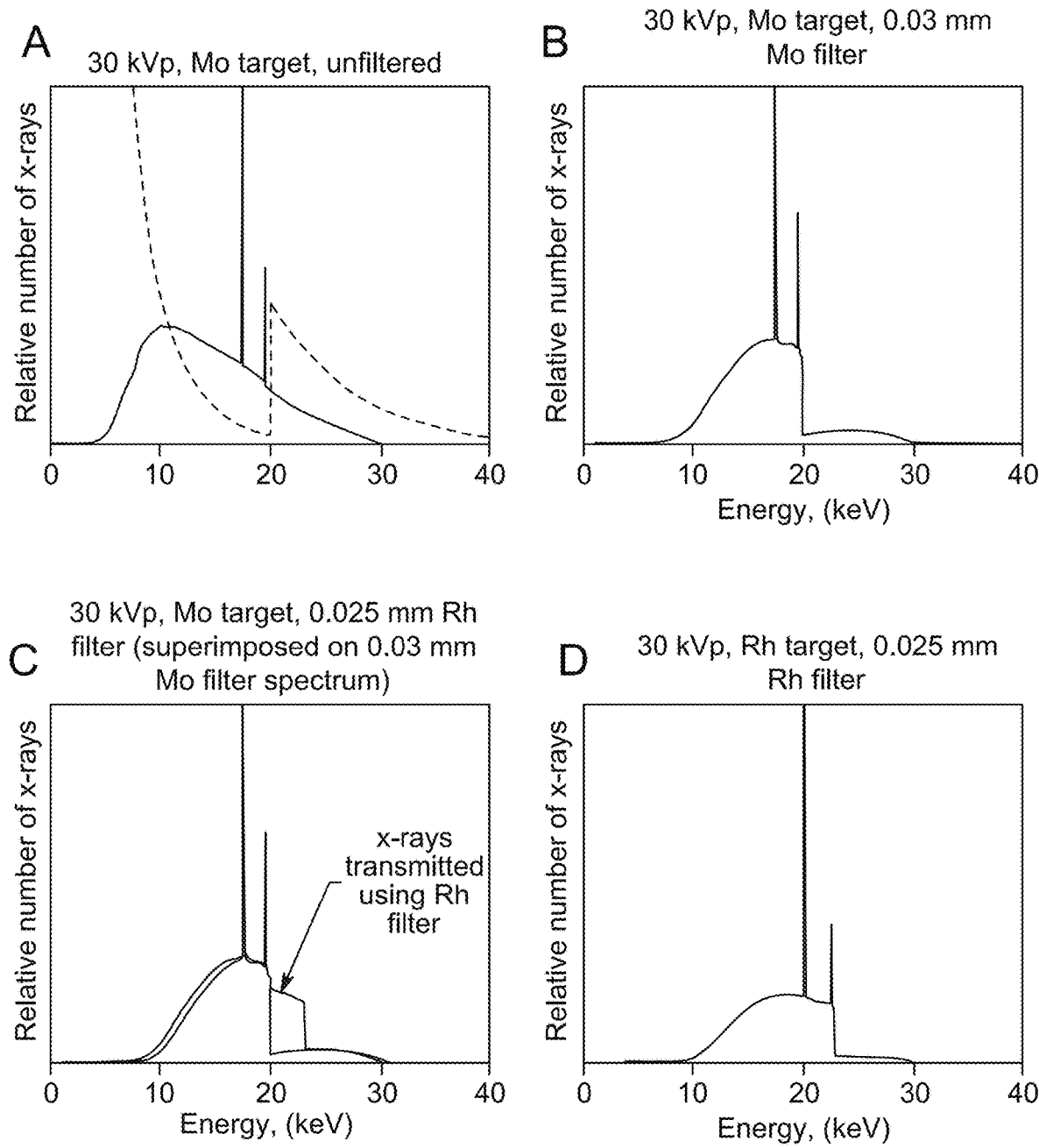
FIG. 7 is an exemplary set of graphs illustrating how x-ray spectra emitted from the x-ray tube can be tailored for diagnostic purposes by filter materials under certain embodiment of the present disclosure.

FIG. 7 illustrates how x-ray spectra emitted from the x-ray tube can be tailored for diagnostic purposes by using different filter materials according to embodiments of the present disclosure. In FIG. 7, spectrum A is an "unfiltered" spectrum of x-ray emitted from a molybdenum target. For other spectra, material combinations for (target, filter) are (Mo, Mo) for spectra B, (Mo, Rh) for spectra C, and (Rh, Rh) for spectrum D, where the acceleration voltage $V_p$ is 30 KV for all cases. Comparing the spectra A and B, (Mo, Mo) combination with B greatly reduces x-rays in both energy ranges higher than 20 KeV and lower than 15 KeV, causing almost no attenuation to the characteristic x-rays. Reduction of high energy X-rays contributes to contrast improvement and a reduction of low energy x-rays prevents high dosage swamping and image contribution. The spectrum B is common for less dense and thinner breast tissues. In the spectrum C, x-rays with some higher energy portions are unfiltered compared with B, this offers more preferable applicability to denser or thicker breast tissues. Similar effects are expected in the spectrum D, (Rh, Rh) combination, where further a higher effective energy than Mo target is realized (see Jerrold, et al., pp. 245-247).

The applicability of x-rays for diagnostics purposes varies with a slight difference in the energy spectra of the x-rays, e.g., due to a slight difference in interactions between x-rays and tissue under examination. However, x-ray images acquired with different energy spectra contain different information of the body under examination. Apparatuses and methods can be used to acquire a plurality of x-ray images of a body under examination with different energy spectra for diagnostic purposes. Consolidation of three or more x-ray images acquired with different energy spectra into a color image for diagnostic purposes greatly aids the ability to identify abnormalities in tissues or objects. The method and system of the present disclosure display colorized images based on a plurality of x-rays obtained at different energy levels and/or using different spectral characteristics as described below together with experimental results demonstrating the effectiveness of the color images.

Figure 8:
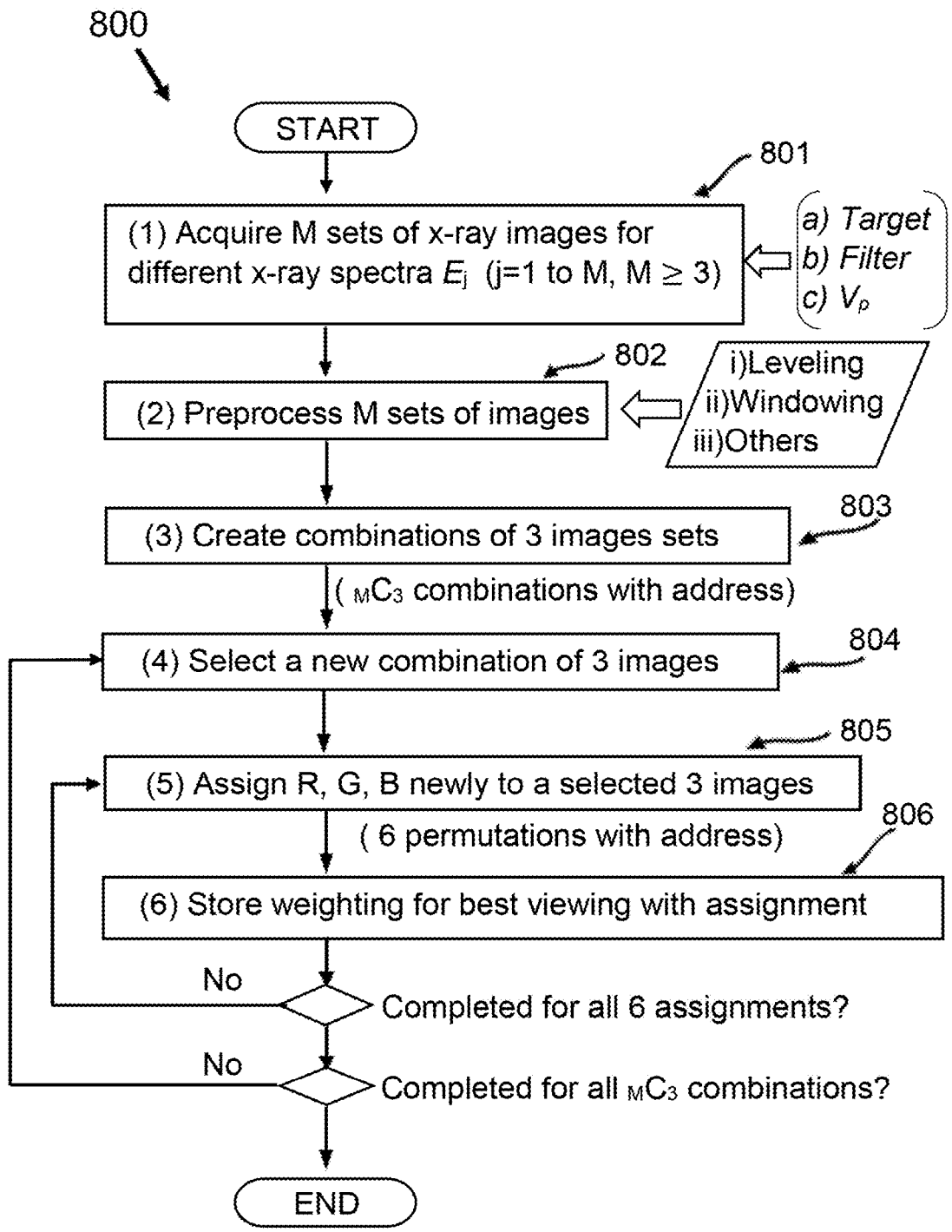
FIG. 8 is an exemplary flowchart illustrating steps for realizing a colored x-ray images based on a plurality sets of x-ray images acquired in gray scale at three or more different energies or with different energy spectra, under certain embodiment of the present disclosure.

FIG. 8 is an exemplary flowchart illustrating steps for obtaining colored (e.g., colorized) x-ray images based on x-ray images acquired in gray scale at three or more different energies or with different energy spectra, according to embodiments of the present disclosure. At the first step 801 of FIG. 8, M (M≥3) sets of x-ray images are acquired in grey scale and in a digital format for x-rays with different energies or different energy spectra. The acquired digital image data are stored in a memory device in a same format. The x-rays with different energies or energy spectra are generated or modified by using (a) different target materials, (b) filters with different materials and thicknesses, (c) different accelerating voltages, and/or (d) combinations of two or all of (a) to (c) above. Conventional x-ray projection images can be acquired for x-rays with different energy spectra generated by either of above options. The x-ray CT images can also be acquired for x-rays with three or more different energy spectra, generated by the combination of (a) and (b) as described above and in FIG. 3.

Ideally the exposure for the different images are taken in an automatic rapid succession to minimize the total exposure time and hence minimize motion artifact and mis-registration. At the second step of the flowchart 802 (FIG. 8), M-sets of the x-ray images acquired in the first step 801 are preprocessed to secure co-registration of images and to enhance contrast in gray scale. Co-registration means that the images taken of the patient correspond to the same geometry and location in a three dimensional space. Mis-registration may generate artifacts if the subject moves during or between successive exposures to generate the different gray-scale images. The mis-registration can be corrected using known methods such as those applied in PET/CT image co-registration techniques. Leveling and Windowing are ways to change the LUT and are preferably included in the step 805. If automatic rapid successive exposure are taken, mis-registration will be minimal for patients. For still objects there should be no mis-registration or motion artifacts.

At the third step 803, combinations of three sets of x-ray images are created from the M-sets of images. There can be $_MC_3$ combinations in selecting the three sets of x-ray images, they are, 1 for M=3, 4 for M=4, 10 for M=5. All combinations are created and stored with series, addresses for the combinations. A combination of the three sets of x-ray images is selected for the fourth step according to the series addresses for the combinations.

At the fourth step 804, three basic colors Red (R), Green (G), and Blue (B) (e.g., primary colors red, yellow and blue; secondary colors green orange and purple; and tertiary colors obtained by combining primary and secondary colors) are assigned to the combination of the three x-ray images selected in the third step 803. There can be six assignments of RGB to the three images. Thus, the six assignments of RGB are generated automatically and stored with series addresses for the six assignments of RGB. An assignment of RBG is selected according to the series addresses for the six assignments of RGB. Then, the three images with the assignment of RGB selected are displayed as a color image in a color display. The color assignment options for each three image spectra gives six times the number of spectra combination $_MC_3$ ($6\times_MC_3$) options for color image formation for M=3, 6 options, for M=4, 24 options, for M=5, 30 options.

At the fifth step 805, modification of RGB colors are adjusted for best viewing is determined by monitoring the color display or through optimization algorithms. The best viewing may vary depending on what specific part of the image will be focused. The modification of RGB is then stored with information on the assignment of RGB and the combination of three sets of x-rays. The modification of the RGB colors can be achieved by mapping the pixel values either through a linear mapping such as windowing and leveling of one or more channels of the RGB image (the channels are the red, green and blue images constituting the RGB image). This linear transformation of the pixel values (PV) is mapping the current pixel values ($PV_{old}$) of each pixel in each channel to a new pixel values ($PV_{new}$) such that $PV_{new}=a\times PV_{old}+b$; where a is scaling factor and b is a shifting factor. The constants a and b may the same or different for each channel of the RGB image. This is effectively multiplying and shifting the pixel values of the red, green and blue images by equal or different values before merging the three modified colors into a new RGB color image. Finally, a more complex modification can be achieved by having a non-liner transformation commonly referred to as Look-Up Table (LUT) for the red, blue or green images before merging them into an RGB color image. For instance, the LUT can have a sigmoid shape in order to enhance the contrast in the middle PV region. These modifications of the red, blue and green channels of an RGB image can effectively produce a very large number of x-ray color images to choose from for best viewing and detection of abnormalities.

The fourth and fifth steps are repeated for all the six assignments of RGB one by one according to the series addresses for the six assignments of RGB created and stored in the fourth step 804. After completion for all the six assignments of RGB for the combination of three images selected in the third step 803, the step returns to the third step 803, and a next combination of three x-ray images is selected according to the series addresses for the combinations. By repeating the steps 804 to 805 for all the combinations of $_MC_3$, all possible combinations of three x-rays and possible assignments of RB are processed. Now color images created for ($_MC_3\times6$) cases for the combination of three x-rays and the assignments of RGB are ready for examination for diagnostics purpose, by displaying either in the tile mode where a plurality of color images are displayed at the same time or in the stack mode where only one of a plurality of color images is displayed and successively replaced.

Figure 9:
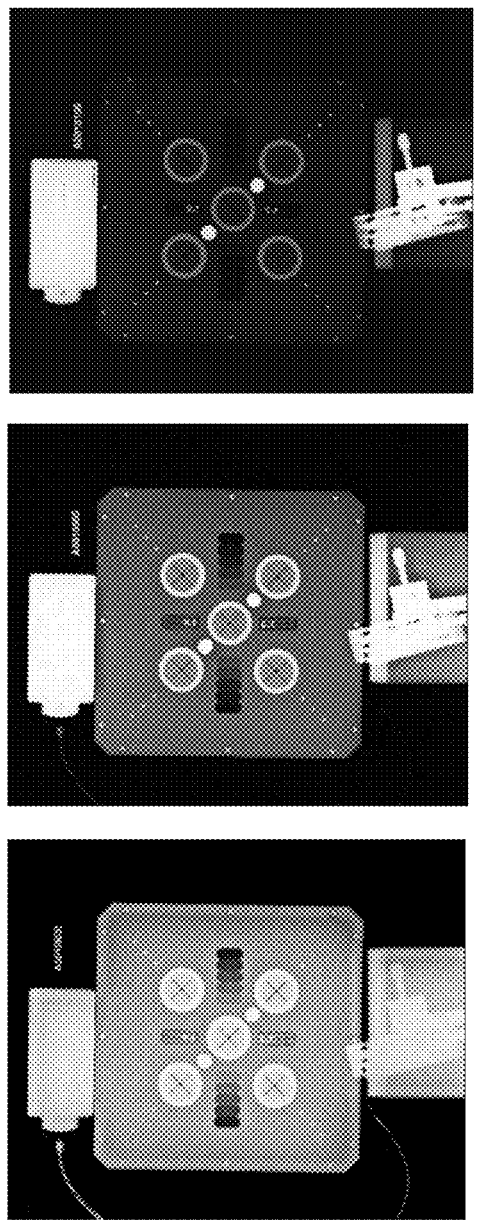
FIG. 9 is an exemplary set of gray scale x-ray images of a phantom acquired with x-rays of different energy spectra, as a part of demonstration of certain embodiment of the present disclosure.

FIG. 9 is an exemplary set of grey scale x-ray images of a phantom acquired with x-rays of different energy spectra, as a part of demonstration according to an embodiment of the present disclosure. The x-rays were generated by a tube with tungsten anode, and with two filter materials of aluminum and copper, by applying different accelerating voltages $V_p$. The images A, B, and C correspond to the acceleration voltages 60, 90 and 110 KV, respectively.

Figure 10A:
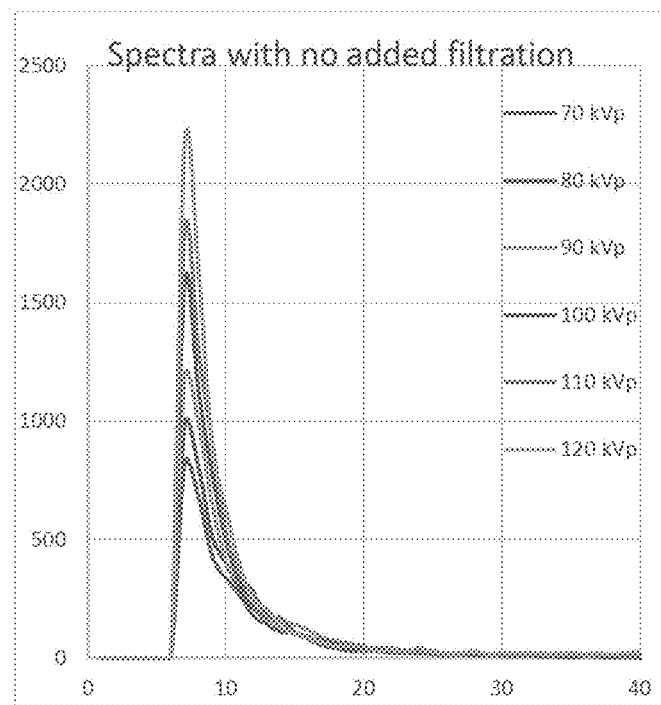
FIG. 10A illustrates x-ray spectra for x-rays used in acquiring images in FIG. 9.
Figure 10B:
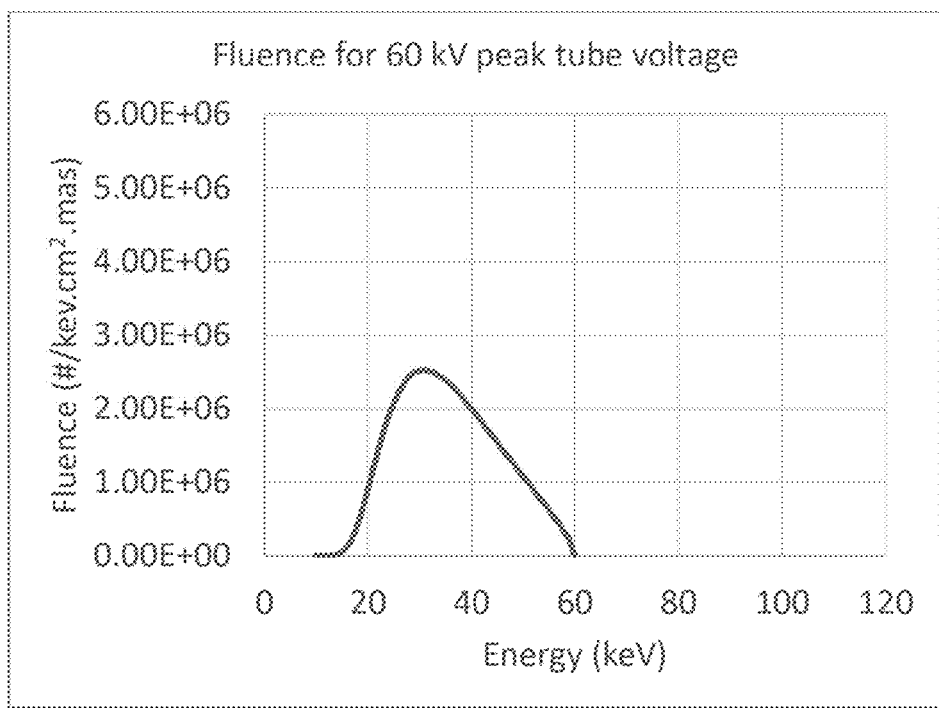
FIG. 10B illustrates simulated x-ray spectra for x-rays used in acquiring images in FIG. 9 using SpecCalc at 60 kV.
Figure 10C:
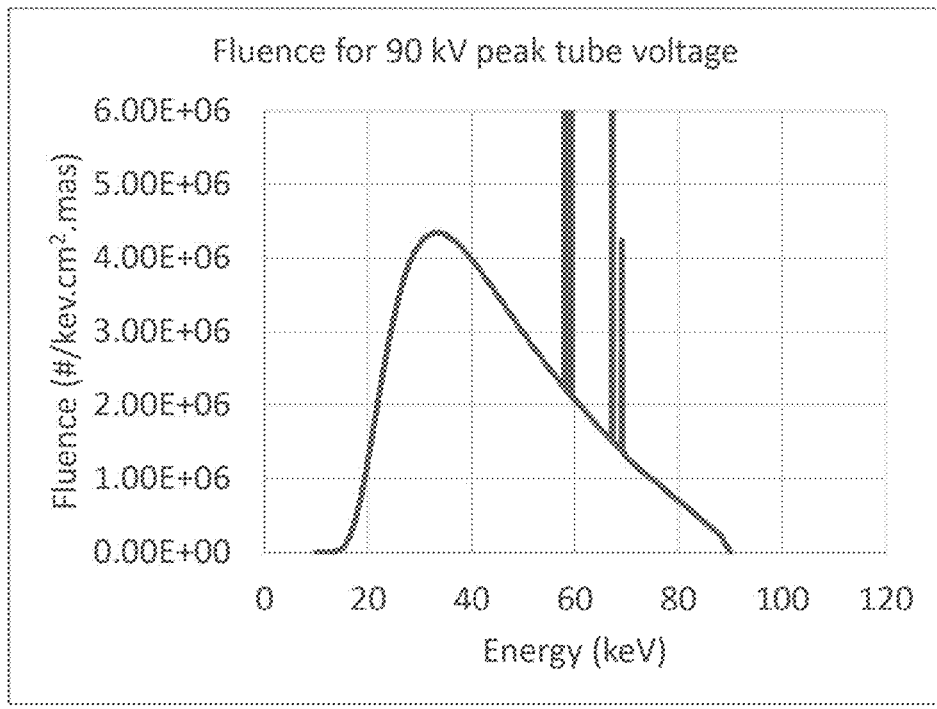
FIG. 10C illustrates simulated x-ray spectra for x-rays used in acquiring images in FIG. 9 using SpecCalc at 90 kV.
Figure 10D:
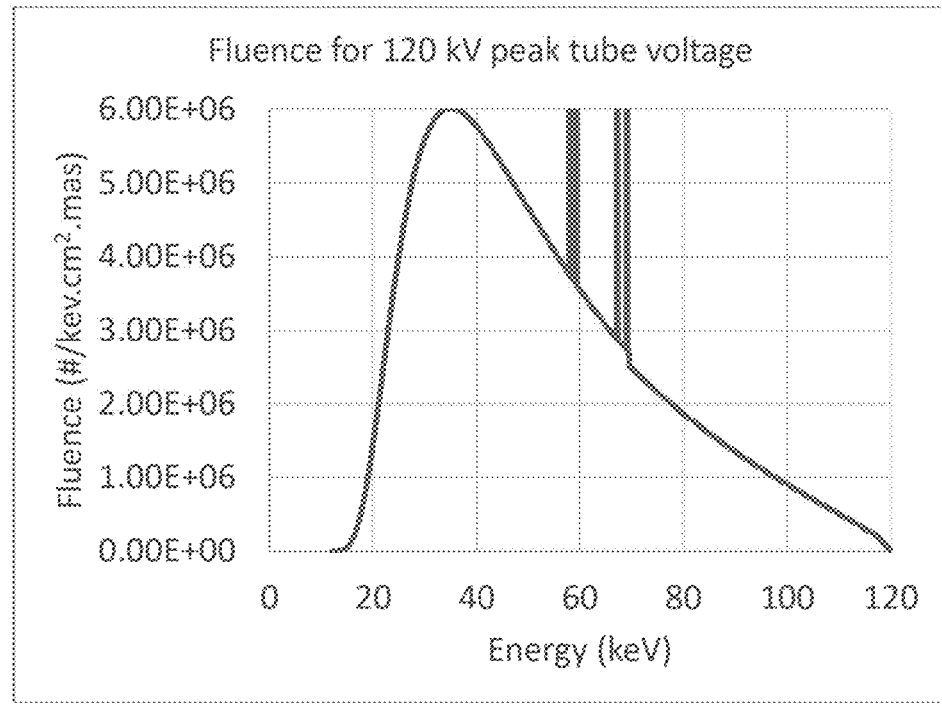
FIG. 10D illustrates simulated x-ray spectra for x-rays used in acquiring images in FIG. 9 using SpecCalc at 120 kV.

FIG. 10A illustrates x-ray spectra for x-rays used in acquiring gray scale images in FIG. 9. FIGS. 10B-D illustrate simulated x-ray spectra for x-rays used in acquiring the gray scale images in FIG. 9 using SpecCalc at 60 kV, 90 kV and 120 kV. As observed here, different x-ray spectra are used to irradiate the phantom by different acceleration voltages and combination with two filters of aluminum and copper.

Figure 11:
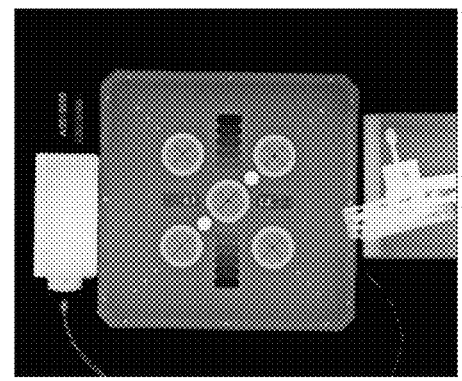
FIG. 11 is an exemplary set of colored x-ray images generated by consolidating the three grey scale images described in FIG. 9 with the method described in FIG. 8, under certain embodiments of the present disclosure.
Figure 11:
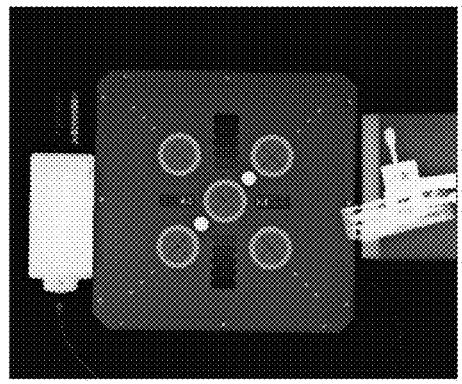
Figure 11:
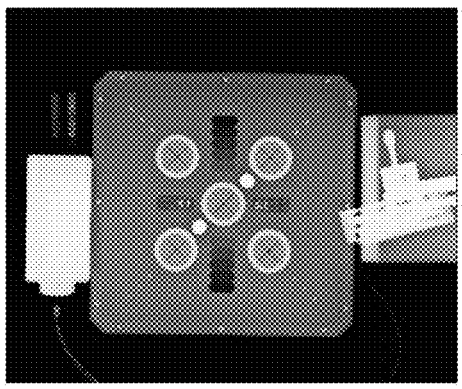

FIG. 11 is an exemplary set of the RB colored x-ray images obtained by consolidating the three grey scale images described in FIG. 9 according to the method described in FIG. 8, according to embodiments of the present disclosure. Here, the assignments of RGB colors to grey scale images acquired at (60 KVp, 90 KVp, 120 KVp) are (R, G, B) in Figure (a), (B, R, G) in Figure (b), (G, B, R) in Figure (c) with no modification of LUT for all three assignments. In this case the red, green and blue images are not modified through any PV transformation.

Comparison of FIG. 11 and FIG. 9 clearly demonstrates that the color images of FIG. 11 obtained by consolidating three grey scale x-ray images of FIG. 9 offer much better conspicuity or differentiation ability than the individual grey scale images. For example, X marks in the five double circles at the center portion in FIG. 11 can be more clearly recognized than those of FIG. 9.

Figure 12:
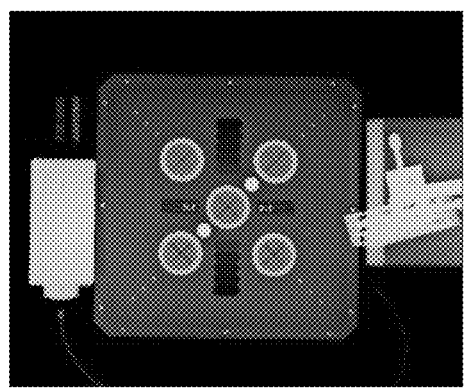
FIG. 12 is an exemplary set of color images for demonstrating effects of the weighting of RGB upon color variations and visibility or differentiation ability of the colored image of FIG. 11(a), under certain embodiment of the present disclosure.
Figure 12:
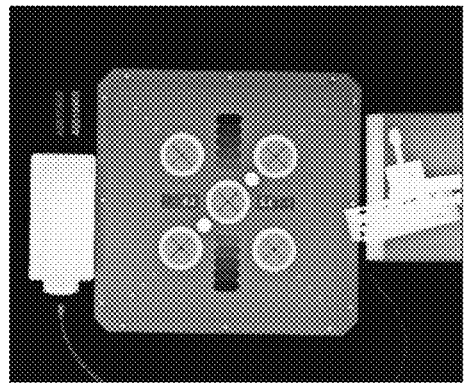
Figure 12:
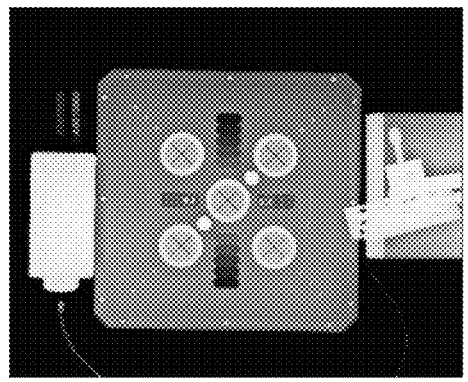

FIG. 12 is an exemplary set of color images for demonstrating effects of the modification of RGB upon color variations using LUT and conspicuity or differentiation ability of the colored image of FIG. 10(a), according to an embodiment of the present disclosure. Here, conspicuity difference among (a), (b) and (c) of FIG. 12 is also confirmed, for example, the fine mesh structure at center bottom portion in (a) is more clearly observed than that in (c). Thus, FIG. 12 also demonstrates that modifying the RGB channels through linear or non-linear LUTs affects not only color variations but also conspicuity and differentiation ability of the colored image. In other words, FIG. 11 demonstrates that adjusting the RGB modification using LUTs can be utilized to improve the differentiation ability of the colored image, in addition to choosing the assignment of RGB with the no modification of RGB channels which was exemplified in FIG. 11.

A method and system for creating x-ray images in color which include the features in the foregoing description provides numerous improvements not only in conventional x-ray projection images but also in x-ray CT images, particularly in improvements of conspicuity or differentiation ability of early phase abnormality of tissues or abnormality in fine portions of object to be diagnosed by x-ray images.

Figure 13:
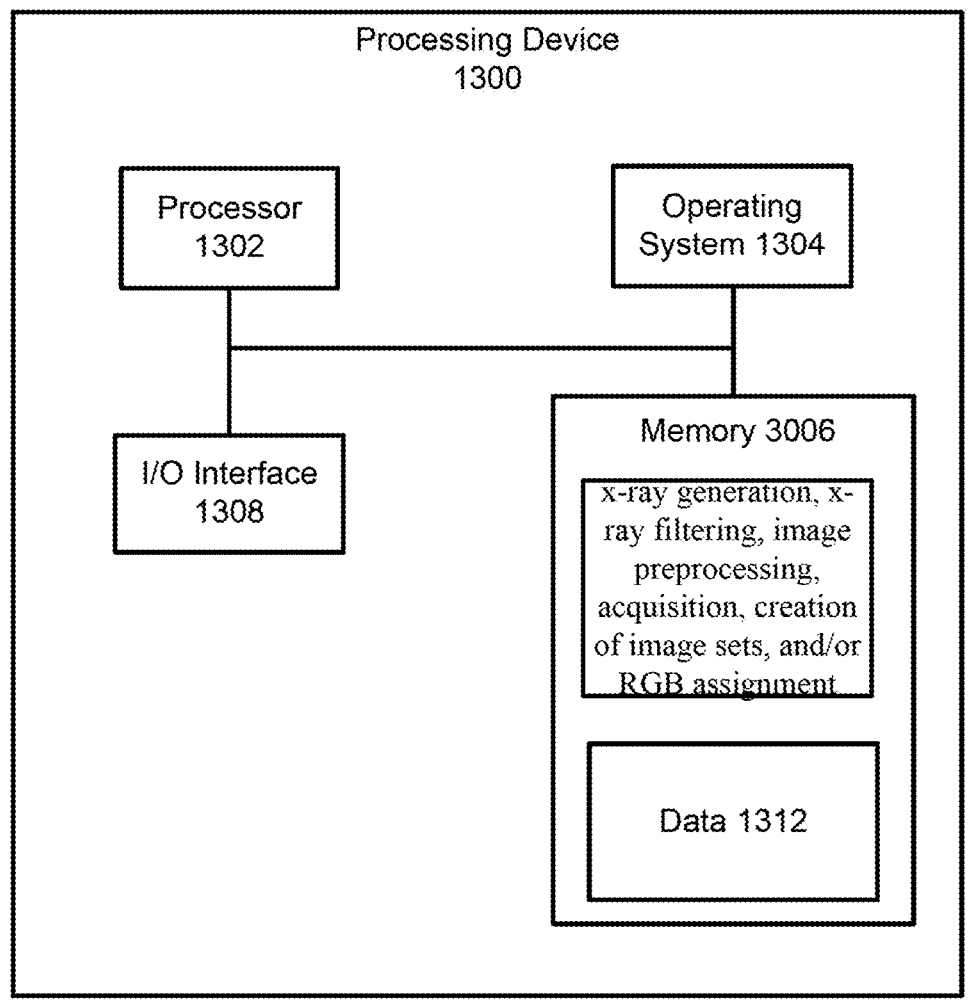
FIG. 13 is a diagram of an example processing device configured for determining color weight and/or for compiling RGB colors representing different grey scale x-ray images at different energies.

FIG. 13 is a block diagram of an example processing device 3000 which may be used to implement one or more features described herein. In one example, device 3000 may be used to implement a computer device including post-acquisition image processing, and perform appropriate method implementations described herein (e.g., x-ray generation, x-ray filtering, image acquisition, post-preprocessing, creation of image sets, RGB assignment, and RGB modification such as described in FIG. 8). Device 3000 can be any suitable computer system, server, or other electronic or hardware device. For example, the device 3000 can be a mainframe computer, desktop computer, workstation, portable computer, or electronic device (portable device, mobile device, cell phone, smart phone, tablet computer, television, TV set top box, personal digital assistant (PDA), media player, game device, wearable device, etc.). In some implementations, device 3000 includes a processor 3002, an operating system 3004, a memory 3006, and input/output (I/O) interface 3008 each in communication with or connected to an x-ray tube.

Processor 3002 can be one or more processors and/or processing circuits to execute program code and control basic operations of the device 3000. A "processor" includes any suitable hardware and/or software system, mechanism or component that processes data, signals or other information. A processor may include a system with a general-purpose central processing unit (CPU), multiple processing units, dedicated circuitry for achieving functionality, or other systems. Processing need not be limited to a particular geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory.

Memory 3006 is typically provided in device 3000 for access by the processor 3002, and may be any suitable processor-readable storage medium, e.g., random access memory (RAM), read-only memory (ROM), Electrical Erasable Read-only Memory (EEPROM), Flash memory, etc., suitable for storing instructions for execution by the processor, and located separate from processor 3002 and/or integrated therewith. Memory 3006 can store software operating on the device 3000 by the processor 3002, including an operating system 704, one or more applications 3010, and messaging/chat session data 3012. In some implementations, applications 3010 can include instructions that enable processor 3002 to perform the functions described herein, e.g., some or all of the tasks of FIG. 8.

Any of software in memory 3004 can alternatively be stored on any other suitable storage location or computer-readable medium. In addition, memory 3004 (and/or other connected storage device(s)) can store compiler extensions, node factory information, and other instructions and data used in the features described herein. Memory 3004 and any other type of storage (magnetic disk, optical disk, magnetic tape, or other tangible media) can be considered "storage" or "storage devices."

I/O interface 3008 can provide functions to enable interfacing the processing device 3000 with other systems and devices such as an x-ray tube or x-ray imaging apparatus. For example, network communication devices, storage devices (e.g., memory and/or database), and input/output devices can communicate via interface 708. In some implementations, the 110 interface 3008 can connect to interface devices including input devices (keyboard, pointing device, touchscreen, microphone, camera, scanner, etc.) and/or output devices (display device, speaker devices, printer, motor, etc.).

For ease of illustration, FIG. 13 shows one block for each of processor 3002, memory 3006, I/O interface 3008, and software block 3010. These blocks may represent one or more processors or processing circuitries, operating systems, memories, I/O interfaces, applications, and/or software modules. In other implementations, device 3000 may not have all of the components shown and/or may have other elements including other types of elements instead of, or in addition to, those shown herein.

In general, a computer that performs the processes described herein (e.g., one or of the tasks of FIG. 8) can include one or more processors and a memory (e.g., a non-transitory computer readable medium). The process data and instructions may be stored in the memory. These processes and instructions may also be stored on a storage medium such as a hard drive (HDD) or portable storage medium or may be stored remotely. Note that each of the functions of the described embodiments may be implemented by one or more processors or processing circuits. A processing circuit can include a programmed processor, as a processor includes circuitry. A processing circuit/circuitry may also include devices such as an application specific integrated circuit (ASIC) and conventional circuit components arranged to perform the recited functions. The processing circuitry can be referred to interchangeably as circuitry throughout the disclosure. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device.

The functions and features described herein may also be executed by various distributed components of a system. For example, one or more processors may execute the functions, wherein the processors are distributed across multiple components communicating in a network. The distributed components may include one or more client and server machines, which may share processing in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes, algorithms and calculations described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for generating an x-ray image in color, the method comprising:
   generating M-sets of x-ray images of a body under examination in gray scale for x-rays with different energy spectra, wherein M is not less than three;
   pre-processing the M-sets of x-ray images including securing co-registration and windowing for a portion in interest in the x-ray images;
   selecting three-sets of x-ray images from the M-sets of x-ray images;
   assigning red (R), green (G), and blue (B) to the three-sets of x-ray images;
   displaying the x-ray image in color with RGB signals generated based on the assigning of RGB to the three-sets of x-ray images,
   wherein the M-sets of x-rays with different energy spectra are generated by a combination of
      a deflection of electron beams impinging an anode in an x-ray tube by a modulation of a control signal applied to a control plate, the control plate configured to deflect the electron beams, and
      a rotation of a filter plate about a center axis of the filter plate with a rotation period, the filter plate aligned adjacent to the anode and outside of the x-ray tube, and configured to receive x-rays emitted from the x-ray tube;
   wherein the anode further comprising a plurality of target tracks comprising different target materials, wherein each of the plurality of target tracks is configured to emit an x-ray with a specific energy spectrum when impinged by the electron beams,
   wherein the filter plate further comprising a plurality of filter sections comprising different filter materials or thicknesses, wherein each of the plurality of filter sections is configured to have a filter section exposure period of the x-rays emitted from the x-ray tube during each cycle of the rotation,
   wherein the modulation of the control signal determines whether to emit any x-ray from either one of the plurality of target tracks with different target materials, or not to generate any x-ray, during the filter section exposure period assigned to each of the plurality of the filter sections within the rotation period, and
   wherein the rotation period of the filter plate is chosen not less than a total sum of the filter section exposure period for each of the plurality of filter sections, and equal to the measurement period assigned to each of the angular positions for the x-ray exposures and data acquisitions in the x-ray CT measurement.

2. The method of claim 1, further comprising:
   selecting a specific modification of the RGB channels through one or more look-up tables (LUT); and
   storing information of the x-ray image in color for the specific LUT modification of RGB, wherein the information comprises the three-sets of x-ray images or identifications thereof, the assigning of RGB to the three sets of x-ray images, and the specific LUT modification of RGB.

3. The method of claim 2, further comprising:

converting the information of the x-ray image into color for the color display to information for a color printing;

storing the information for the color printing; and printing an x-ray picture in color based on the information for the color printing using either RGB or CMYK colors.

4. The method of claim 1, wherein the generating includes modification of an acceleration voltage, or modification of combinations of different target materials and different filter materials or thicknesses.

5. The method of claim 4, wherein the different target materials comprises at least one of Tungsten, Molybdenum, or Rhodium, and the different filter materials comprises at least one of Tungsten, Molybdenum, Rhodium, Aluminum, Copper, or Beryllium.

6. The method of claim 1, wherein the M-sets of x-ray images are projection images.

7. The method of claim 1, wherein the M-sets of x-ray images are computed tomographic (CT) images of a body under examination, wherein generating the M-sets of x-ray images further includes, acquiring output data of an x-ray detector for x-rays traversed a body under examination, for M-sets of x-rays with different energy spectra, at each of angular positions required for x-ray exposures and data acquisitions in an x-ray CT measurement, and within a measurement period assigned to each of the angular positions for the x-ray exposures and data acquisitions in the x-ray CT measurement.

* * * * *